US00PP12387P2

(12) United States Plant Patent
Zerr

(10) Patent No.: US PP12,387 P2
(45) Date of Patent: Feb. 5, 2002

(54) POINSETTIA PLANT NAMED 'FISNOVA'

(75) Inventor: Katharina Zerr, Simmern (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/210,111

(22) Filed: Dec. 11, 1998

(51) Int. Cl.[7] ..... A01H 5/00
(52) U.S. Cl. ..... Plt./307
(58) Field of Search ..... Plt./307

(56) References Cited

U.S. PATENT DOCUMENTS 4,724,276 A * 2/1988 Ecke, Jr. ..... 47/58
PP9,336 P * 10/1995 Beckmann ..... Plt./306

FOREIGN PATENT DOCUMENTS

CA 97-1191 12/1997
DE EUP 205 12/1997
EP 98/1410 10/1998

OTHER PUBLICATIONS

Fischer USA catalogue, p. 4 (1998).

UPOV–ROM GTITM Computer Database 1999/02, GTI JOUVE Retrieval Software, citations for 'Fisnova', May 1999.*

* cited by examiner

*Primary Examiner*—Bruce R. Campell
*Assistant Examiner*—Michelle Kizilkaya
(74) *Attorney, Agent, or Firm*—Foley & Lardner

(57) ABSTRACT

'Fisnova' is characterized by medium to dark-red bract color which are medium-sized, ovate, and weakly to moderately lobed; dark-green foliage which is ovate-shaped with weak lobes; early flowering response; and medium growth resulting in a medium tall and relatively compact plant habit during the vegetative stage of growth.

1 Drawing Sheet

BACKGROUND OF THE INVENTION

The present invention relates to a new and distinct cultivar of Poinsettia plant known by the cultivar name 'Fisnova' and botanically known as *Euphorbia pulcherrima.*

'Fisnova' is a product of a planned breeding program which had the objective of creating new poinsettia cultivars with red bract color, dark-green foliage, good branching characteristics, and early flowering response. 'Fisnova' was originated from a hybridization made in a controlled breeding program in Hillscheid, Germany, in 1994.

The female parent was a proprietary hybrid seedling No. S90-502-1 characterized by red bract color, dark-green foliage and early-flowering. The male parent was a proprietary hybrid seedling No. S90-1202-1 with bright-red bract color, medium-green foliage and very compact habit. 'Fisnova' was discovered and selected as one flowering plant (No. 3736) within the progeny of the stated parentage by Katharina Zerr in autumn of 1995 in a controlled environment in Hillscheid, Germany.

The seeds from the hybridization made in February 1995 and the seedlings produced therefrom were identified by numbers. In summer of 1995, a cutting was taken from each seedling and grown as a flowering, single-stem plant for examination in the autumn and winter. The cuttings used were new grown shoot tips from the upper area of the plant, taken from branches emerging from the main stem higher than the place of the grafting. After plant no. 3736 was selected, more cuttings were taken from the original seedling and grafted onto rootstocks of variety 'Beckmanns Altrosa' (U.S. Plant Pat. No. 9,336) in order to transmit the branching-causing agent, phytoplasma, into the clone to improve the branching characteristics. From cuttings of these grafted plants, branched plants were grown for trial cultivation (horticultural examination) in autumn and winter of 1996 to 1997. Horticultural examination initiated in autumn of 1996 and continuing thereafter has demonstrated that the combination of characteristics as herein disclosed for 'Fisnova' are firmly fixed and are retained through successive generations of asexual reproduction.

BRIEF DESCRIPTION OF THE INVENTION

The following traits have been repeatedly observed and are determined to be basic characteristics of 'Fisnova' which in combination distinguish this Poinsettia as a new and distinct cultivar:

1. Medium to dark-red bract color.
2. Medium-sized ovate bracts, weakly to moderately lobed;
3. Dark-green foliage, ovate-shaped with weak lobes;
4. Early flowering response; and
5. Medium growth, medium tall and relatively compact habit during vegetative stage.

'Fisnova' has not been observed under all possible environmental conditions. The phenotype may vary significantly with variations in environment such as temperature, light intensity, and daylength without a change in genotype. The following observations, measurements and comparisons describe plants grown in Langley, British Columbia, Canada, under greenhouse conditions which approximate those generally used in commercial practice.

Of the many commercial varieties known to the inventor, the most similar in comparison to 'Fisnova' are the patented cultivars 'Freedom Red' (U.S. Plant Pat. No. 7,825) and 'Fiscor' (U.S. Plant Pat. No. 9,364). In comparison to 'Freedom Red', 'Fisnova' has somewhat more intense and more stable red-colored bracts, which do not tend to fade at high temperature, and which have a smoother surface. Bracts and leaves of 'Fisnova' are narrower in size than with 'Freedom Red'. In comparison to 'Fiscor', 'Fisnova' has a different plant habit, taller and less wide, and has an earlier flowering response.

'Fisnova' can also be compared to the cultivars 'Fismille' (U.S. Plant patent application Ser. No. 09/210,122) and 'Fisgala' (U.S. Plant patent application Ser. No. 09/210,123). Chart A shows a comparison of 'Fisnova', 'Fismille' and 'Fisgala'.

CHART A

| | 'FISNOVA' | 'FISMILLE' | 'FISGALA' |
|---|---|---|---|
| Bract color: | Medium to dark red; upper surface: RHS 46B lower surface: RHS 46B to 46C | Brilliant, medium-red; upper surface: RHS 45A lower surface: RHS 46B | Dark-red, often more bluish than: upper surface: RHS 46B lower surface: RHS 46B |
| Stem color: | Light to medium green, RHS 137C; weak infusion of anthocyanin | Medium-green, RHS 137B; weak infusion of anthocyanin | Medium-green, RHS 137B; strong infusion of anthocyanin |
| Foliage, lobes | Weak | Almost no lobes | Weak to medium |
| Growth/ Plant habit | Medium vigor, relatively compact as a young plant, develops later a more round plant habit when given enough space so that all the branches may develop fairly evenly | vigorous, medium to tall, upright plant habit | Moderately vigorous growth, medium height, V-shaped plant habit with uniformly developed branches |
| No. of branches | 8.5 | 6.9 | 7.5 |
| Start of flowering | 8.5 weeks | 7.5 weeks | 8–8.5 weeks |

BRIEF DESCRIPTION OF THE DRAWING

The accompanying color photographs sheet shows typical inflorescence and foliage of a mature potted plant of 'Fisnova', with colors being as true as possible with illustrations of this type.

DETAILED BOTANICAL DESCRIPTION

The plants described were grown in a greenhouse in Langley, British Columbia, Canada, in autumn of 1997. Rooted cuttings were planted into 15-cm pots on August 1, and were pinched on August 18, leaving 8 nodes. The minimum temperature was 23° C. until October 10, 20° C. to mid-November, and lower thereafter. The plants initiated flowers under natural short-day conditions in autumn.

In the following description, color references are made to The Royal Horticultural Society Colour Chart (R.H.S.). The color values were determined indoors in a north light.

Classification:

*Botanical.*—*Euphorbia pulcherrima.*

*Commercial.*—Poinsettia, cv. 'Fisnova'.

Parentage:

*Female parent.*—Hybrid seedling No. S90-502-1.

*Male parent.*—Hybrid seedling No. S90-1202-1.

Plant:

*Form.*—Shrub, self-branching.

*Growth habit.*—Medium vigor, plant habit of branched plants in medium tall (of medium height), but relatively compact (dense, branches and leaves). Height, including pot, if 45 cm. The average number of branches is 8.5.

*Stem color.*—Light to medium-green, RHS 137 C, with a weak, reddish-brown infusion of anthocyanin.

*Rooting.*—Relatively fast, about 20 days.

*Blooming habit.*—Flowering response time under natural short-day conditions in autumn: botanically, cyathia open, in late November; commercially, bracts colored and marketable, about November 24.

*Flowering response time.*—About 8.5 weeks.

*Keeping quality of bracts and leaves ('shelf life').*—Approximately 25 days. Relatively good, average or medium for the group of dark-foliage varieties.

Foliage:

*Number of leaves per plant.*—Approximately 32–36.

*Shape.*—Ovate, with slightly rounded base, acuminated tip, and weak lobes.

*Margin.*—Entire.

*Texture.*—Upper surface: Smooth and flat, only weakly veined, veins hardly visible, RHS 146 D, basal part of midrib may have the same reddish coloring as the petiole. Lower surface: Flat and smooth, except for the slightly protruding midrib and finer side veins, which are arranged in a herringbone pattern; the vein color is light-green, RHS 139 D, in parts dull pink, RHS 180 D.

*Size.*—Leaf blade length is 14.2 cm; leaf blade width is 10.4 cm; petiole length is 7.5 cm.

*Color.*—Generally a uniform dark-green. Mature foliage: upper surface is RHS 139 A; under surface is RHS 137 B. New foliage: upper side is about RHS 144 A; under side is about RHS 137 D.

*Petiole color.*—Dark-red, near RHS 53 A.

*Aspect.*—Petioles and leaves are horizontally directed.

*Disease resistance.*—Typical, no special observation made.

Flowering description:

*Inflorescence.*—Medium-sized, horizontally directed, with the bracts relatively smooth and flat. The diameter of inflorescence is 26 cm.

*Inflorescence per plant.*—6.7 to 7.

*Bracts per inflorescence.*—9 to 11 true bracts, each over 2 cm long.

*Size of bract.*—The length is 14.5 cm and width is 10.3 cm; petiole is 2.3 cm.

*Bracts, shape.*—Ovate-shaped with rounded base, acuminated tip, and weakly to moderately lobed.

*Texture.*—Flat and smooth, the veins, arranged in a herringbone pattern, are hardly visible on the upper surface; the vein color of the upper side corresponds closely to the bract color or appears slightly darker, while on lower surface, the veins are usually lighter, brownish pink, RHS 47 A or lighter.

*Color.*—Generally a uniform medium-red. Upper surface: Near RHS 46 B, or slightly more bluish. Lower surface: More bluish than RHS 46 B to 46 C.

*Petiole, color.*—Dark-red, near RHS 46 A.

*Cyathia.*—Few, about 5–10 in number, borne in a narrow cluster, about 20 mm wide; diameter of the single cythium is 5–6 mm.

*Color.*—Light to medium green, RHS 143 B, with darker, medium-green patches, about RHS 137 D; top is red, about RHS 46 C.

*Retention.*—Medium, better than "Freedom Red".

*Nectar cups.*—Small to medium-sized, bright yellow, margin usually without anthocyanin coloring.

Reproductive organs:

*Stamens.*—Red filaments, fertile, yellow pollen.

*Pistils.*—Style and stigma are red, 6-lobed stigma.

*Ovaries.*—Triangular, 3 ovules.

Seed/fruit set: Few seeds are formed spontaneously, but fertile when pollinated; shape and development is typical for the species.

I claim:

1. A new and distinct poinsettia plant named 'Fisnova', substantially as illustrated and described.

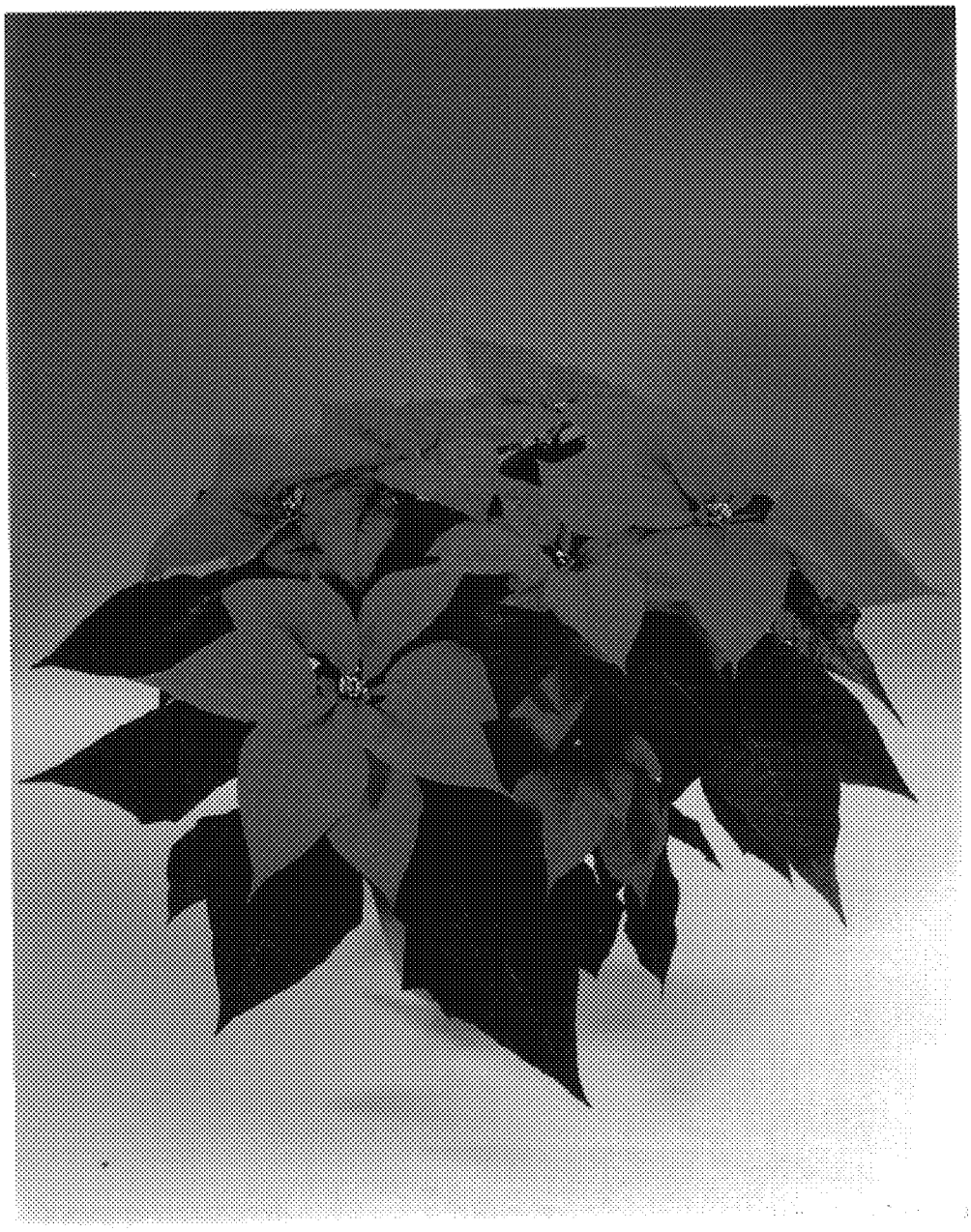

* * * * *